(12) United States Patent
Sakano et al.

(10) Patent No.: US 8,439,885 B2
(45) Date of Patent: May 14, 2013

(54) DISPOSABLE DIAPER HAVING A STOOL PASSING OPENING

(75) Inventors: Katsushi Sakano, Kasugai (JP); Izumi Tashiro, Tokyo (JP); Katsuhiko Sugiyama, Tokyo (JP); Kahori Suzuki, Tokyo (JP)

(73) Assignees: Oji Nepia Co., Ltd., Tokyo (JP); Oji Paper Co., Ltd., Tokyo (JP)

( * ) Notice: Subject to any disclaimer, the term of this patent is extended or adjusted under 35 U.S.C. 154(b) by 1244 days.

(21) Appl. No.: 11/545,726

(22) Filed: Oct. 10, 2006

(65) Prior Publication Data

US 2007/0088305 A1 Apr. 19, 2007

(30) Foreign Application Priority Data

Oct. 14, 2005 (JP) ................................. 2005-300375

(51) Int. Cl.
*A61F 5/452* (2006.01)
*A61F 13/512* (2006.01)

(52) U.S. Cl.
USPC ... 604/350; 604/348; 604/385.19; 604/385.101

(58) Field of Classification Search ............. 604/385.19, 604/348, 350, 383, 385.101, 385.28
See application file for complete search history.

(56) References Cited

U.S. PATENT DOCUMENTS

| | | | | |
|---|---|---|---|---|
| 2,625,160 A | * | 1/1953 | Maxim | 604/348 |
| 3,447,536 A | * | 6/1969 | Snyder | 604/348 |
| 3,532,093 A | * | 10/1970 | Lovret | 604/348 |
| 3,559,648 A | * | 2/1971 | Mason, Jr. | 604/375 |
| 3,729,004 A | * | 4/1973 | Burger | 604/394 |
| 4,609,518 A | * | 9/1986 | Curro et al. | 264/504 |
| 4,629,643 A | * | 12/1986 | Curro et al. | 428/131 |
| 4,676,785 A | * | 6/1987 | Battista | 604/369 |
| 4,892,536 A | * | 1/1990 | DesMarais et al. | 604/385.27 |
| 4,990,147 A | * | 2/1991 | Freeland | 604/385.22 |
| 5,037,413 A | * | 8/1991 | Haque | 604/385.19 |
| 5,062,840 A | * | 11/1991 | Holt et al. | 604/385.19 |
| 5,171,236 A | * | 12/1992 | Dreier et al. | 604/369 |
| 5,207,663 A | * | 5/1993 | McQueen | 604/385.05 |
| 5,397,316 A | * | 3/1995 | LaVon et al. | 604/369 |
| 5,397,318 A | * | 3/1995 | Dreier | 604/385.19 |
| 5,554,142 A | * | 9/1996 | Dreier et al. | 604/385.23 |
| 5,554,149 A | * | 9/1996 | O'Donnell | 604/385.19 |
| 5,558,660 A | * | 9/1996 | Dreier | 604/385.19 |
| 5,648,142 A | * | 7/1997 | Phillips | 428/132 |
| 5,653,703 A | * | 8/1997 | Roe et al. | 604/385.01 |

(Continued)

FOREIGN PATENT DOCUMENTS

| | | |
|---|---|---|
| GB | 2 268 073 | 1/1994 |
| JP | 2559050 | 9/1997 |
| JP | 2002-011044 | 1/2002 |

*Primary Examiner* — Melanie Hand
*Assistant Examiner* — Paula Craig
(74) *Attorney, Agent, or Firm* — Burr & Brown (57) ABSTRACT

A disposable diaper is provided, including an absorber, a top sheet disposed to cover the upper surface of the absorber and at least partially formed of a liquid permeable material, a back sheet disposed to cover the lower surface of the absorber and formed of a liquid impermeable material, and a skin contact sheet disposed above the top sheet and formed with a stool passing opening capable of passing a stool therethrough. The stool passing opening is formed into such a shape that a posterior region posterior to a centerline in the anteroposterior direction of the stool passing opening is smaller in the opening area than an anterior region anterior to the centerline.

14 Claims, 8 Drawing Sheets

U.S. PATENT DOCUMENTS

| | | | |
|---|---|---|---|
| 5,792,130 A * | 8/1998 | Widlund et al. | 604/385.01 |
| 5,843,065 A * | 12/1998 | Wyant | 604/385.09 |
| 6,010,490 A * | 1/2000 | Freeland et al. | 604/385.19 |
| 6,022,607 A * | 2/2000 | James et al. | 428/131 |
| 6,120,485 A * | 9/2000 | Gustafsson et al. | 604/385.19 |
| 6,132,409 A * | 10/2000 | Vogt et al. | 604/348 |
| 6,248,098 B1 * | 6/2001 | Sayama | 604/385.28 |
| 6,262,331 B1 * | 7/2001 | Nakahata et al. | 604/383 |
| 6,291,050 B1 * | 9/2001 | Cree et al. | 428/131 |
| 6,375,643 B1 * | 4/2002 | Moorhead et al. | 604/322 |
| 6,406,465 B1 * | 6/2002 | Otsubo | 604/385.01 |
| 6,409,711 B1 * | 6/2002 | Jonbrink | 604/385.01 |
| 6,423,884 B1 * | 7/2002 | Oehmen | 604/369 |
| 6,458,114 B1 * | 10/2002 | Mishima et al. | 604/385.24 |
| 6,471,681 B1 * | 10/2002 | Ronnberg et al. | 604/385.19 |
| 6,482,191 B1 * | 11/2002 | Roe et al. | 604/385.01 |
| 6,562,015 B1 * | 5/2003 | Wilson | 604/385.01 |
| 6,595,972 B1 * | 7/2003 | Wise et al. | 604/385.01 |
| 6,699,228 B1 * | 3/2004 | Chmielewski et al. | 604/385.28 |
| 6,951,552 B2 * | 10/2005 | D'Acchioli et al. | 604/319 |
| 7,329,794 B2 * | 2/2008 | Van Gompel et al. | 604/378 |
| 7,566,330 B2 * | 7/2009 | Sugiyama et al. | 604/385.28 |
| 7,785,310 B2 * | 8/2010 | Sakano et al. | 604/385.101 |
| 8,066,683 B2 * | 11/2011 | Sugiyama et al. | 604/385.101 |
| 8,211,076 B2 * | 7/2012 | Sugiyama et al. | 604/385.28 |
| 2002/0010453 A1 * | 1/2002 | Mishima et al. | 604/385.19 |
| 2002/0013567 A1 * | 1/2002 | Mishima et al. | 604/385.101 |
| 2002/0133132 A1 * | 9/2002 | Copat et al. | 604/383 |
| 2002/0173763 A1 * | 11/2002 | Tsuji et al. | 604/385.19 |
| 2003/0114816 A1 * | 6/2003 | Underhill et al. | 604/378 |
| 2004/0039363 A1 | 2/2004 | Sugiyama et al. | |
| 2005/0182382 A1 * | 8/2005 | Bailey | 604/385.101 |
| 2006/0135931 A1 * | 6/2006 | Suzuki et al. | 604/385.19 |
| 2006/0142727 A1 * | 6/2006 | Suzuki et al. | 604/385.19 |
| 2006/0149207 A1 * | 7/2006 | Turi et al. | 604/385.19 |
| 2007/0088302 A1 * | 4/2007 | Sugiyama et al. | 604/378 |
| 2007/0088304 A1 * | 4/2007 | Sakano et al. | 604/385.19 |
| 2007/0088306 A1 * | 4/2007 | Sugiyama et al. | 604/385.19 |
| 2007/0088310 A1 * | 4/2007 | Sugiyama et al. | 604/385.101 |

* cited by examiner

DISPOSABLE DIAPER HAVING A STOOL PASSING OPENING

This application claims priority to Japanese Application No. 2005-300375 filed Oct. 14, 2005.

BACKGROUND OF THE INVENTION

1. Field of the Invention

The present invention relates to a disposable diaper including an absorber, a top sheet, a back sheet, and a skin contact sheet which is disposed above the top sheet and formed with an opening capable of passing a stool therethrough.

2. Description of the Related Art

In recent years, as a diaper for an infant or an elderly or disabled person, there has been a widely used a disposable diaper which includes an absorber, a top sheet disposed to cover the upper surface of the absorber and at least partially formed of a liquid permeable material, and a back sheet disposed to cover the lower surface of the absorber and formed of a liquid impermeable material. This disposable diaper is used in such a manner that a surface of the top sheet is applied to contact the skin of a wearer of the disposable diaper. Thereby, the urine discharged by the wearer penetrates through the top sheet and is absorbed and retained by the absorber. Further, the back sheet having good leakage preventing performance prevents the leakage of the excrement to the outside of the diaper.

In the disposable diaper of the above-described structure, however, the urine penetrates through the top sheet but most of the stool does not penetrate through the top sheet and thus remains thereon. The stool remaining on the top sheet adheres to the crotch or the buttocks of the wearer. This requires a troublesome wiping work which increases the burden of child rearing or nursing care, and also causes skin trouble to the wearer. Such phenomenon becomes more prominent when the stool discharged by the wearer is an unformed stool.

In view of this, another type of disposable diapers has been proposed in which another sheet member (hereinafter referred to as a "skin contact sheet" in the present specification) is disposed above the top sheet (see Paragraph 0010 and FIG. 2 of Japanese Registered Utility Model No. 2559050, and Paragraph 0020 and FIG. 1 of Japanese Unexamined Patent Application Publication No. 2002-11044, for example). These disposable diapers are structured such that the skin contact sheet is formed with an opening capable of passing the stool therethrough (i.e., a stool passing opening) for causing the stool discharged by the wearer to drop on the top sheet through the stool passing opening.

According to the above-described disposable diaper, the skin contact sheet first contacts the skin of the wearer. Thus, the top sheet disposed under the skin contact sheet does not easily come into direct contact with the skin of the wearer. That is, the skin of the wearer is separated from the top sheet. This also means that a shielding layer, i.e., the skin contact sheet intervenes between the top sheet and the skin of the wearer. Therefore, even if the stool remains on the top sheet, the effect of substantially decreasing the chance of direct contact of the stool with the skin of the wearer can be expected.

Even in the disposable diaper having the skin contact sheet, however, the stool once dropped on the top sheet through the skin contact sheet adheres to the buttocks of the wearer in some cases. That is, the disposable diaper is not satisfactory enough in the effective prevention of the adherence of the stool to the buttocks of the wearer, and thus is still open to improvement.

SUMMARY OF THE INVENTION

As described above, a disposable diaper capable of effectively preventing the adherence of the stool to the buttocks of the wearer has not yet been disclosed so far, and thus has been longed for. In view of the conventional techniques as described above, it is an object of the present invention to provide a disposable diaper capable of effectively preventing the stool once dropped on the top sheet through the skin contact sheet from adhering to the buttocks of the wearer.

The present inventors conducted a keen examination to improve the above-described conventional techniques and obtained a finding that, when the stool once dropped on the top sheet through the skin contact sheet adheres to the buttocks of the wearer, the adherence of the stool tends to be along the gluteal groove (i.e., the cleft of the buttocks) of the wearer. Then, the present inventors completed the present invention with the idea of improving the shape of the stool passing opening formed on the skin contact sheet to improve the above-described conventional techniques. Specifically, the present invention provides the following disposable diaper.

A disposable diaper according to a first aspect of the present invention includes an absorber, a top sheet disposed to cover an upper surface of the absorber and at least partially formed of a liquid permeable material, a back sheet disposed to cover a lower surface, of the absorber and formed of a liquid impermeable material, and a skin contact sheet disposed above the top sheet and formed with an opening capable of passing a stool therethrough (i.e., a stool passing opening). The stool passing opening is formed into such a shape that a region posterior to a centerline in the anteroposterior direction of the stool passing opening (i.e., a posterior region) is smaller in the opening area than a region anterior to the centerline (i.e., an anterior region).

According to a second aspect of the present invention, in the disposable diaper according to the first aspect of the present invention, the stool passing opening may be formed into such a shape that the anterior region includes a portion in which the opening width of the stool passing opening is the greatest (i.e., a maximum opening portion).

According to a third aspect of the present invention, in the disposable diaper according to the second aspect of the present invention, the stool passing opening may be formed into such a shape that the opening width decreases from the maximum opening portion toward a rear end of the stool passing opening.

According to a fourth aspect of the present invention, in the disposable diaper according to the third aspect of the present invention, the stool passing opening may be formed into such a shape that the decrease rate of the opening width is large in a segment from the maximum opening portion to a predetermined point (i.e., an inflection point) and small in a segment from the inflection point to the rear end.

According to a fifth aspect of the present invention, in the disposable diaper according to either one of the third and fourth aspects of the present invention, the stool passing opening may be formed into such a shape that the opening width decreases at a constant rate from the maximum opening portion to the rear end.

According to a sixth aspect of the present invention, in the disposable diaper according to any one of the first to fifth aspects of the present invention, the stool passing opening may be formed into such a shape that a hole is combined with a slit, and that the slit is formed to connect with a back body side of the hole.

According to a seventh aspect of the present invention, in the disposable diaper according to any one of the second to sixth aspects of the present invention, the stool passing opening may be formed such that the maximum opening portion is located at a position corresponding to the position of the anus of a wearer of the disposable diaper.

The disposable diaper according to the present invention is capable of effectively preventing the stool once dropped on the top sheet through the skin contact sheet from adhering to the buttocks of the wearer.

DETAILED DESCRIPTION OF THE INVENTION

Specific description will now be made of preferred embodiments of the disposable diaper according to the present invention, taking a two-piece-type and pants-type diaper as an example. The present invention, however, widely includes disposable diapers which have particular features of the invention, and thus is not limited to the following embodiments. For drawing convenience, leg-surrounding stretchable members are eliminated from the drawing of FIG. 3.

Figure 1:
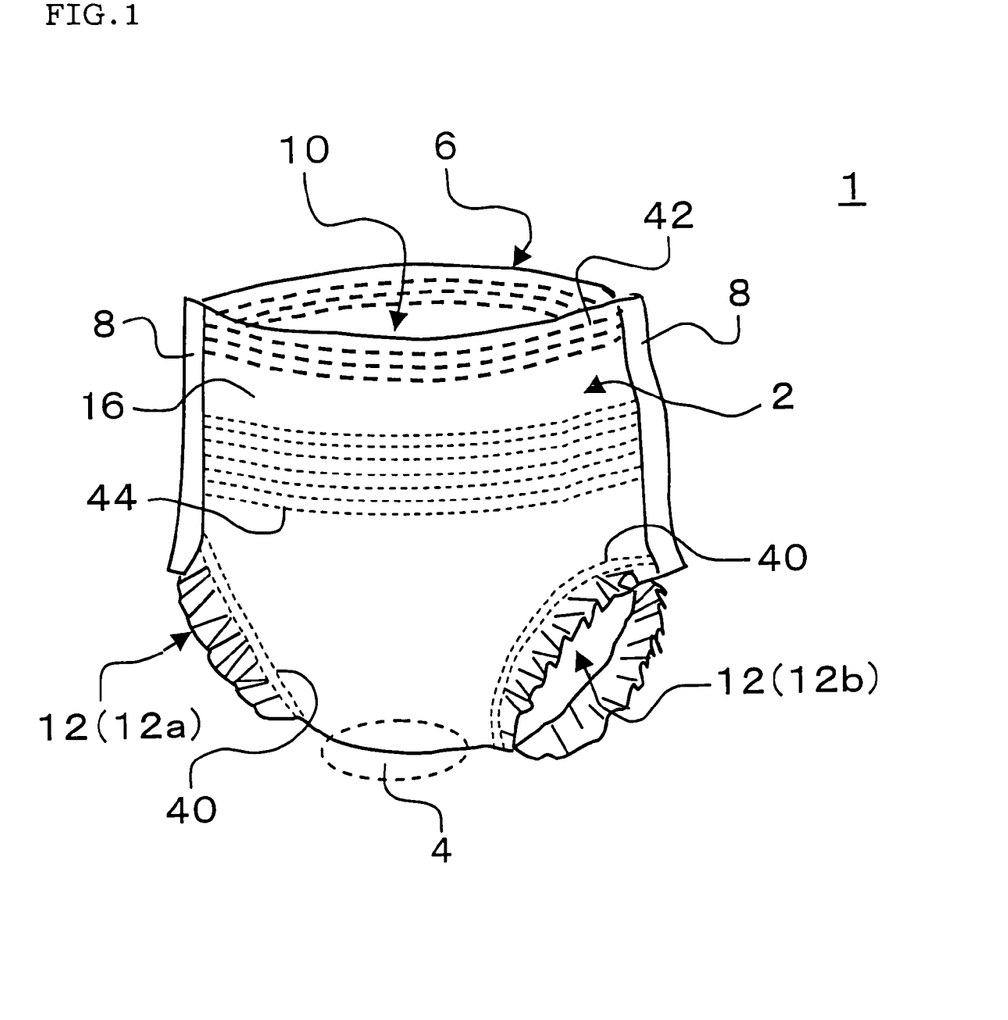
FIG. 1 is a schematic perspective view illustrating one embodiment of the disposable diaper according to the present invention, as viewed from the front side of the diaper.
Figure 2:
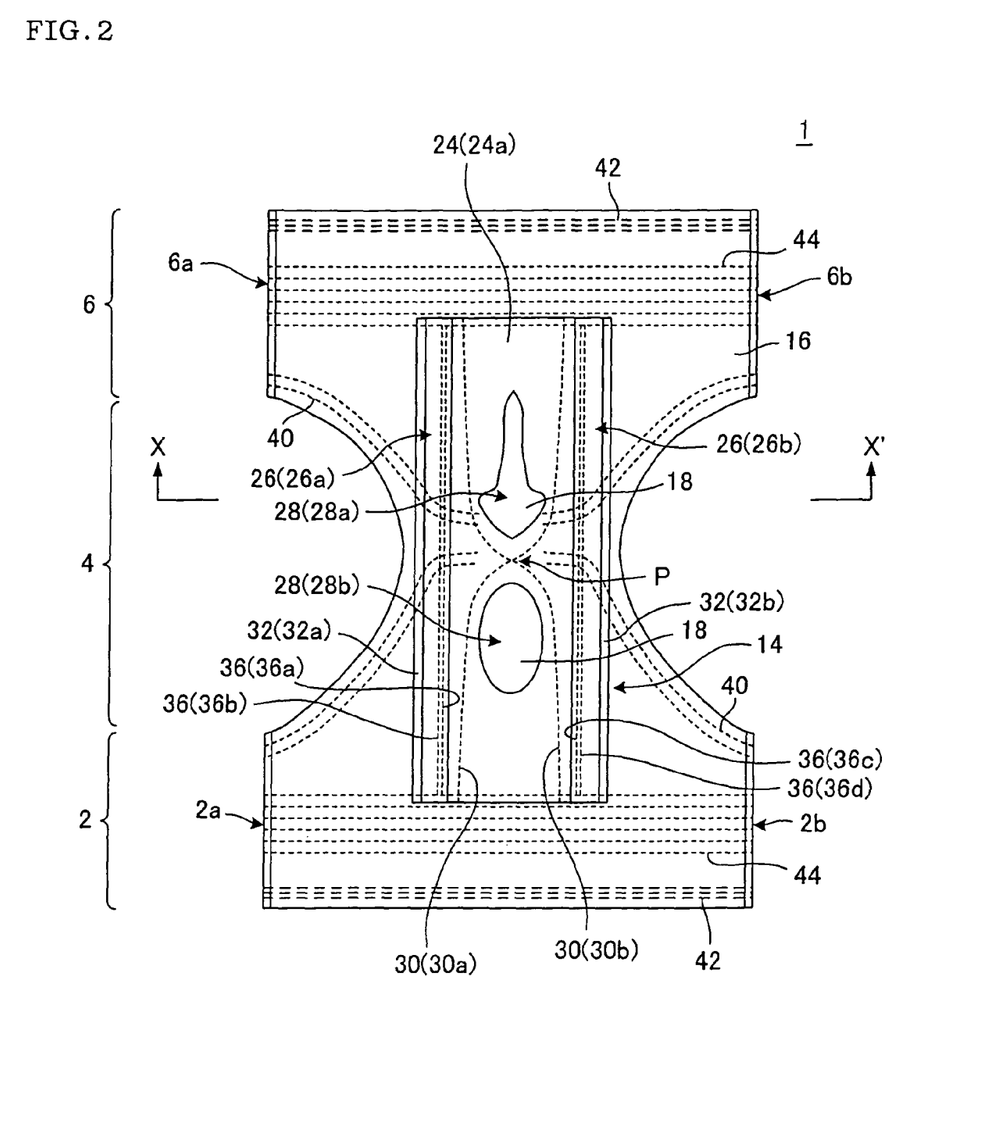
FIG. 2 is a plan view illustrating the one embodiment of the disposable diaper according to the present invention, as viewed from the side of the absorbent member of the disposable diaper when the diaper shown in FIG. 1 is unfolded.
Figure 3:
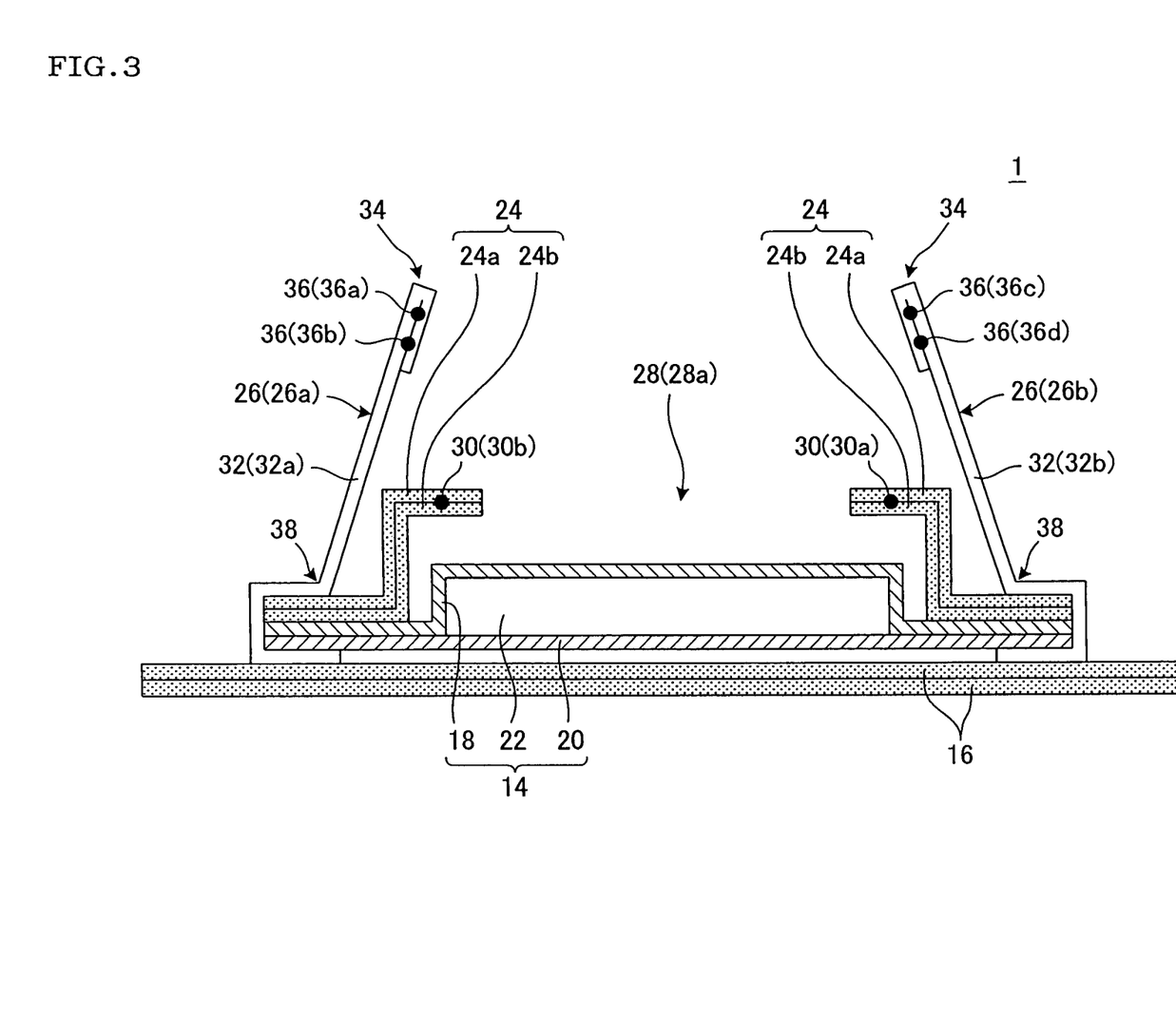
FIG. 3 is a schematic cross-sectional view illustrating the one embodiment of the disposable diaper according to the present invention, as cut along the X-X' line in the disposable diaper shown in FIG. 2.

In the present specification, the "pants-type diaper" refers to a diaper preformed into a pants shape, as in the case of a disposable diaper 1 illustrated in FIGS. 1 and 2, in which corresponding side edges of a front body part 2 and a back body part 6 (i.e., side edges 2a and 6a and side edges 2b and 6b) are joined together to form joining parts 8, a waist-surrounding opening 10, and a pair of leg-surrounding openings 12a and 12b. Further, the "two-piece-type diaper" refers to a type of diaper which includes an absorbent member 14 having a function of absorbing and retaining the excrement of a wearer of the diaper (i.e., an absorbing and retaining function) and an exterior covering member 16 having a function of covering the body of the wearer (i.e., a fitting function), and in which the absorbent member 14 is disposed on the inside of the exterior covering member 16. As illustrated in FIG. 3, the absorbent member 14 is a member including, as component parts thereof, an absorber 22, a top sheet 18, and a back sheet 20.

Further, in the present specification, the "front body part," the "crotch part," and the "back body part" refer to a part covering the ventral part (i.e., the front side of the body) of a wearer when the diaper is applied to the wearer, a part covering the crotch of a wearer when the diaper is applied to the wearer, and a part covering the dorsal part (i.e., the back side of the body) of a wearer when the diaper is applied to the wearer, respectively.

[1] The structure of the disposable diaper according to the present invention: As in the case of the disposable diaper 1 illustrated in FIGS. 1 to 4, the disposable diaper according to the present invention is a disposable diaper including the absorber 22, the top sheet 18, and the back sheet 20. The disposable diaper further includes a skin contact sheet 24 which is disposed above the top sheet 18 and is formed with an opening capable of passing the stool therethrough (i.e., a stool passing opening 28a). The stool passing opening 28a is formed into such a shape that a region posterior to a centerline Lc in the anteroposterior direction of the stool passing opening 28a (i.e., a posterior region 48) is smaller in the opening area than a region anterior to the centerline Lc (i.e., an anterior region 46).

[1-1] The skin contact sheet: The skin contact sheet is a member for separating the skin of the wearer from the top sheet, and is a sheet-shaped member disposed above the top sheet and formed with an opening capable of passing the stool therethrough (i.e., a stool passing opening). With the provision of the skin contact sheet, the skin of the wearer first contacts the skin contact sheet, and thus the top sheet disposed under the skin contact sheet does not easily come into direct contact with the skin of the wearer. That is, the skin of the wearer is separated from the top sheet. This also means that a shielding layer, i.e., the skin contact sheet intervenes between the top sheet and the skin of the wearer. Therefore, even if the stool remains on the top sheet, the effect of substantially decreasing the chance of direct contact of the stool with the skin of the wearer is obtained.

As the material forming the skin contact sheet, a nonwoven fabric, a mesh sheet, a film, or the like made of such a resin as polyethylene, polypropylene, and polyester can be used, for example. In particular, it is preferable to use the nonwoven fabric for the good texture against the skin. The above-described materials may be liquid permeable, liquid impermeable, or water repellent. It is preferable, however, that the above-described materials are water repellent materials (e.g., a water repellent nonwoven fabric) for the ability to maintain a dry texture (i.e., dryness) even after a long time wearing.

The skin contact sheet of the disposable diaper according to the present invention needs to be formed with the opening capable of passing therethrough the stool discharged by the wearer (i.e., the stool passing opening). With this structure, the stool discharged by the wearer drops on the top sheet through the skin contact sheet, and thus the chance of direct contact of the stool with the skin of the wearer can be substantially decreased.

Meanwhile, according to the conventional disposable diaper having the skin contact sheet, the stool discharged by the wearer adheres to the buttocks of the wearer in some cases, even if the stool has dropped on the top sheet through the skin contact sheet. It has been confirmed that the adherence of the stool in such a case tends to be along the gluteal groove (i.e., the cleft of buttocks) of the wearer. The present inventors found from further examination of this phenomenon that, in such a state in which the wearer is in a recumbent position on his back, the entire diaper is pressed to contact the skin of the wearer, and the stool discharged by the wearer flows along the gluteal groove, which is an clearance gap, toward the back of the wearer (i.e., toward the back body part of the diaper). Accordingly, the stool adheres along the gluteal groove of the wearer, depending on the opening extent of the stool passing opening.

Figure 4:
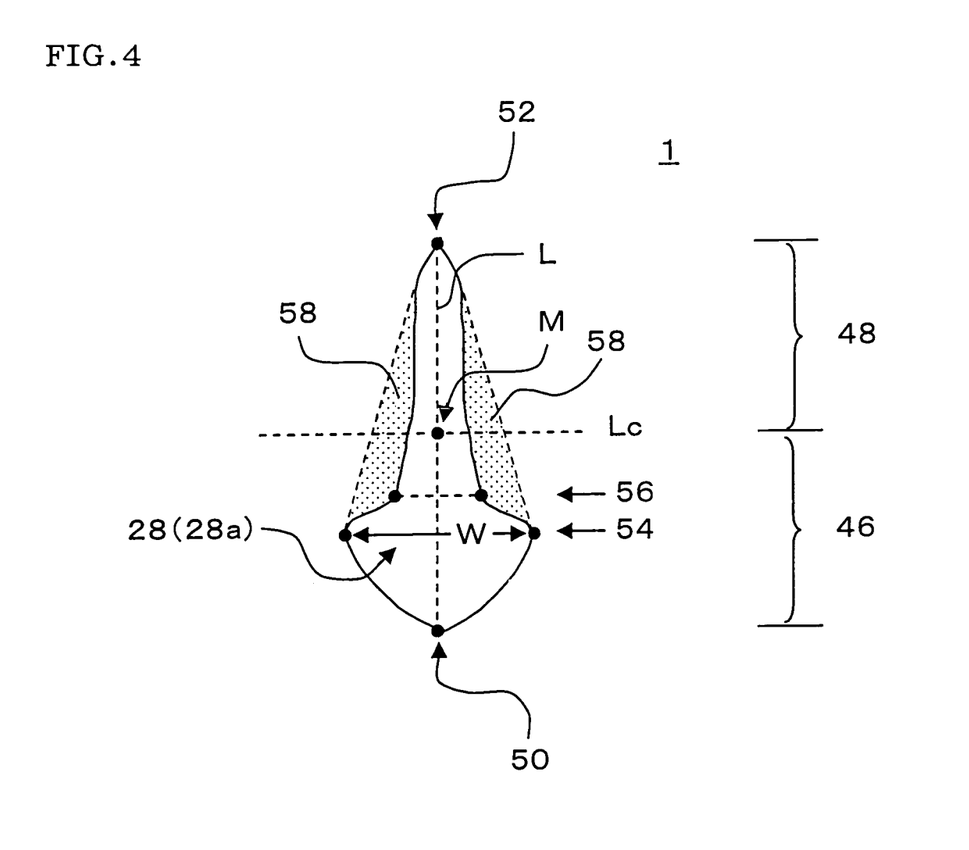
FIG. 4 is a partially enlarged view illustrating the one embodiment of the disposable diaper according to the present invention, enlarging the stool passing opening of the disposable diaper shown in FIG. 2.

In light of the above, as illustrated in FIG. 4, in the disposable diaper according to the present invention, the stool passing opening 28a is formed into such a shape that the region posterior to the centerline Lc in the anteroposterior direction of the stool passing opening 28a (i.e., the posterior region 48) is smaller in the opening area than the region anterior to the centerline Lc (i.e., the anterior region 46).

In the conventional disposable diaper, the stool passing opening is generally formed into a shape which is symmetrical and equal in the opening area in the anteroposterior and lateral directions, such as a circular shape, an oval shape, and a rhombic shape. As described above, however, if the opening area of the posterior region is reduced, the adherence of the stool to the gluteal groove can be minimized, even if the stool discharged by the wearer flows along the gluteal groove toward the back of the wearer. It is therefore possible to effectively prevent the stool once dropped on the top sheet through the skin contact sheet from adhering to the buttocks, particularly to the gluteal groove, of the wearer. Meanwhile, the opening area of the anterior region is kept large, and thus the passage of the stool is not interrupted.

In the present specification, the "the centerline in the anteroposterior direction" refers to a straight line extending in the lateral direction of the diaper from a midpoint M of a straight line L which connects a front end 50 and a rear end 52 of the stool passing opening 28a, as in the case of the centerline Lc illustrated in FIG. 4.

It is preferable in the disposable diaper according to the present invention that the stool passing opening is formed into such a shape that the anterior region includes a portion in which the opening width of the stool passing opening is the greatest (i.e., a maximum opening portion). With this shape, the stool can easily pass through the anterior region, while the stool is prevented from adhering to the gluteal groove in the posterior region.

For example, in the disposable diaper 1 illustrated in FIGS. 2 and 4, the stool passing opening 28a has an approximately anchor shape, in which the anterior region 46 includes a portion with laterally projecting outer edges. In the disposable diaper 1, this projecting portion is the portion in which the opening width W is the greatest (i.e., a maximum opening portion 54), and the anterior region 46 includes the maximum opening portion 54.

Further, it is preferable in the disposable diaper according to the present invention that the stool passing opening is formed into such a shape that the opening width decreases from the maximum opening portion toward the rear end. This is because, if the stool passing opening is formed into such a shape that the opening width increases again in a region from the maximum opening portion to the rear end (e.g., a calabash shape), there arises a possibility of adherence of the stool in the area with the increased opening width, even if the opening width does not reach the greatest value.

For example, in the disposable diaper 1 illustrated in FIGS. 2 and 4, the stool passing opening 28a is formed into such a shape that the opening width W does not increase again but decreases in the region from the maximum opening portion 54 to the rear end 52 of the stool passing opening 28a. That is, this is an example in which the stool passing opening 28a is formed into such a shape that the opening width W decreases from the maximum opening portion 54 toward the rear end 52.

Further, it is preferable in the disposable diaper according to the present invention that the stool passing opening is formed into such a shape that the decrease rate of the opening width is large in a segment from the maximum opening portion to a predetermined point (i.e., an inflection point) and small in a segment from the inflection point to the rear end.

For example, the disposable diaper 1 illustrated in FIGS. 2 and 4 is an example in which the stool passing opening 28a is formed into such a shape that the opening width W remarkably decreases (i.e., the decrease rate of the opening width W is large) in a segment from the maximum opening portion 54, in which the outer edges laterally protrude, to a predetermined point (i.e., an inflection point 56), and that the opening width W gently decreases (i.e., the decrease rate of the opening width W is small) in a segment from the inflection point 56 to the rear end 52. With this shape, flap portions 58 are formed at the side edges of the stool passing opening 28a, and the flap portions 58 block the stool dropped on the top sheet 18. Thus, the adherence of the stool to the wearer can be more effectively prevented.

In the disposable diaper according to the present invention, however, the stool passing opening may be formed into such a shape that the opening width decreases at a constant rate from the maximum opening portion to the rear end.

Figure 5:
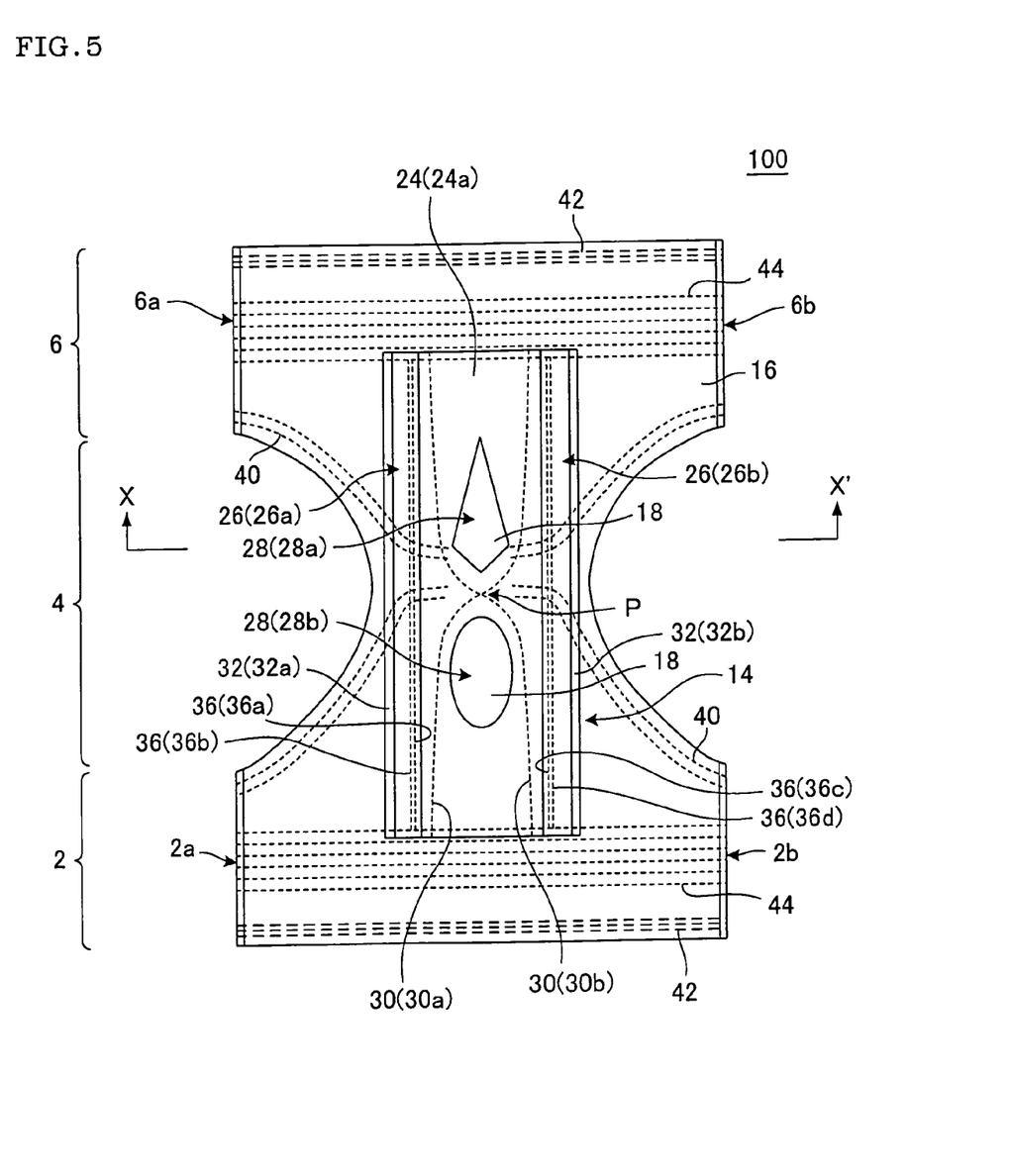
FIG. 5 is a plan view illustrating another embodiment of the disposable diaper according to the present invention, as viewed from the side of an absorbent member of the disposable diaper when the diaper is unfolded.
Figure 6:
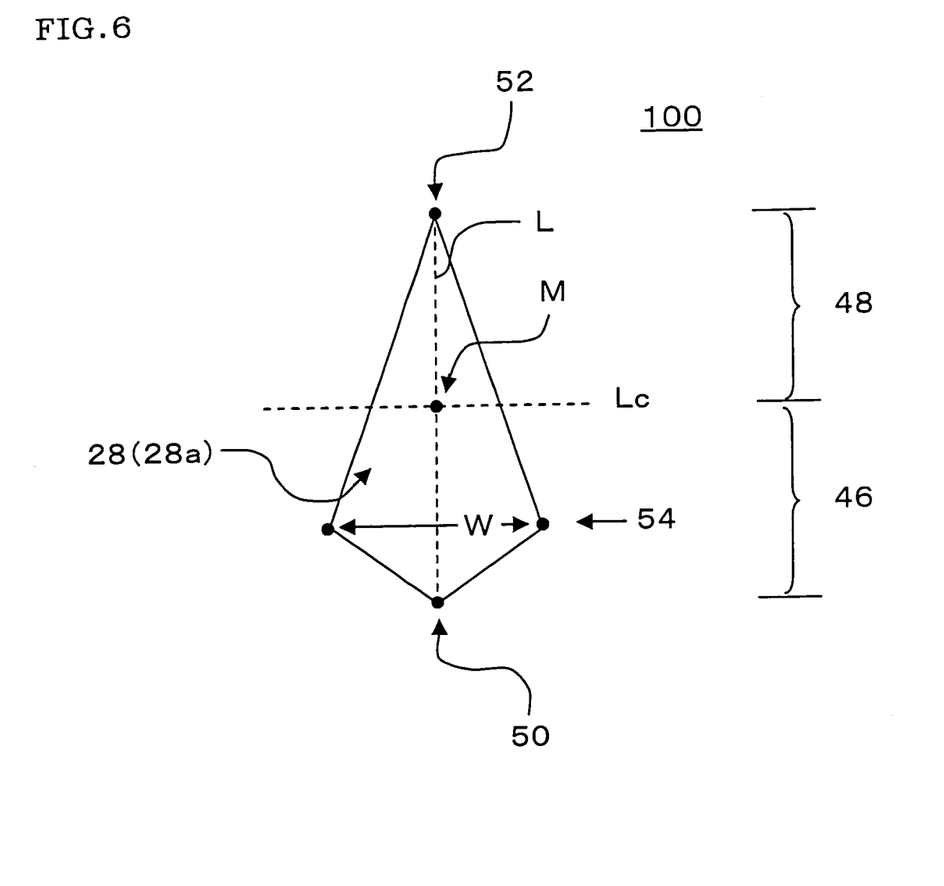
FIG. 6 is a partially enlarged view illustrating the another embodiment of the disposable diaper according to the present invention, enlarging the stool passing opening of the disposable diaper shown in FIG. 5.

For example, in a disposable diaper 100 illustrated in FIGS. 5 and 6, the stool passing opening 28a has a decentered rhombic shape in which the opening width W decreases at a constant rate from the maximum opening portion 54 to the rear end 52. With this shape, the flap portions are not formed at the side edges of the stool passing opening 28a. This is advantageous in that the shape of the opening is stable. Further, if the flap portions are formed, the flop portions may open upward depending on the arrangement of opening stretchable members, and the wearing feel of the diaper may be deteriorated. With the above-described shape, however, such inconvenience is not caused.

There is no particular restriction on the shape of the stool passing opening, as long as the shape allows the passage of the stool. That is, the "opening" capable of passing the stool therethrough includes the so-called opening (i.e., a hole) such as a circular opening, an oval opening, and a rhombic opening, and also includes a slit such as a straight-line slit, a cross-shape slit, and a star-shape slit formed by crossing three or more slits. Therefore, a hole and a slit may be combined to form an opening in which the opening area is smaller in the posterior region than in the anterior region. Specifically, in a preferable embodiment, the stool passing opening may have such a shape that a hole and a slit are combined and that the slit is formed to connect with the back body side of the hole.

Figure 7:
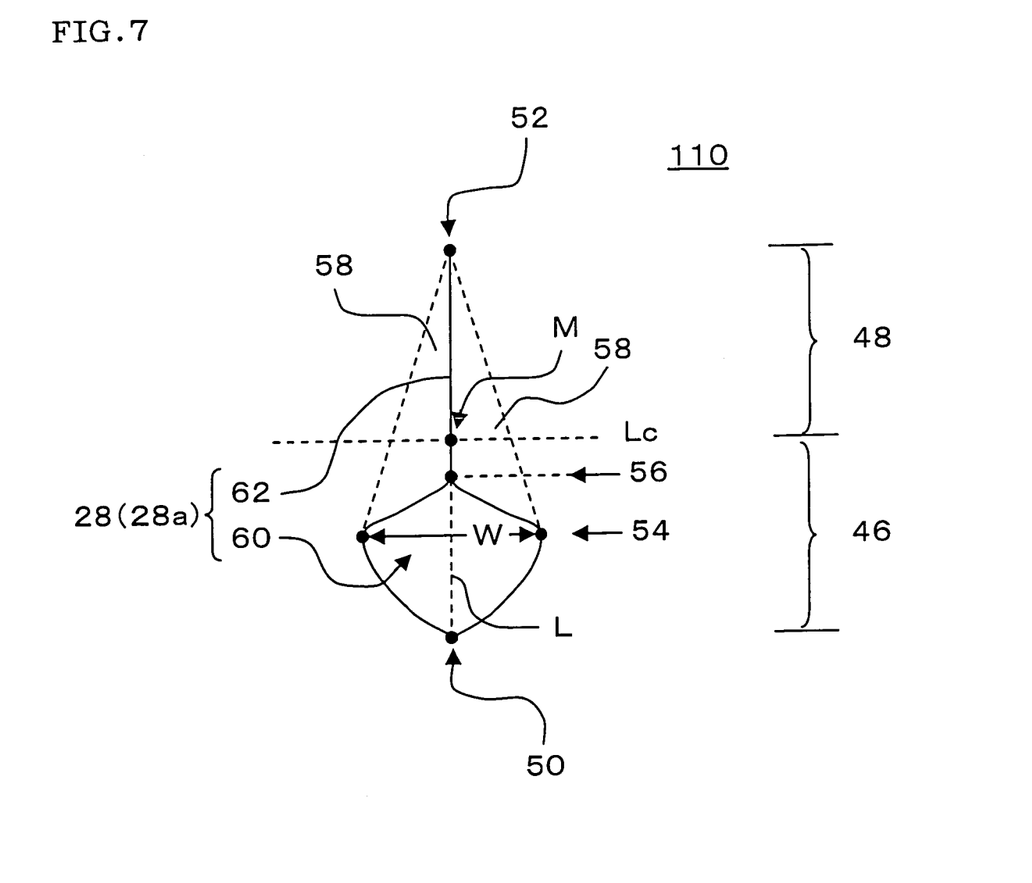
FIG. 7 is a partially enlarged view illustrating still another embodiment of the disposable diaper according to the present invention, enlarging the stool passing opening of the disposable diaper.

For example, in a disposable diaper 110 illustrated in FIG. 7, the stool passing opening 28a has such a shape that a hole 60 and a slit 62 are combined and that the slit 62 is formed to connect with the back body side of the hole 60. In the stool passing opening 28a, the anterior region 46 includes the maximum opening portion 54, and the opening width W remarkably decreases in the segment from the maximum opening portion 54 to the inflection point 56, while the opening width W is zero in the segment from the inflection point 56 to the rear end 52. That is, the present stool passing opening 28*a* is a particular example of the opening in which the opening area of the posterior region 48 is zero and thus is smaller than the opening area of the anterior region 46.

As in the case of the disposable diaper 1 illustrated in FIG. 4, the flap portions 58 are formed at the side edges of the stool passing opening 28*a* also in the disposable diaper 110 illustrated in FIG. 7. Thus, the adherence of the stool to the wearer can be effectively prevented. Further, unlike the disposable diaper 1 illustrated in FIG. 4, the posterior region 48 of the stool passing opening 28*a* has the opening area of zero. Therefore, the stool is almost completely blocked by the flap portions 58 after the stool has once dropped on the top sheet 18 through the stool passing opening 28*a*. Accordingly, the adherence of the stool to the buttocks of the wearer can be more effectively prevented.

Figure 8:
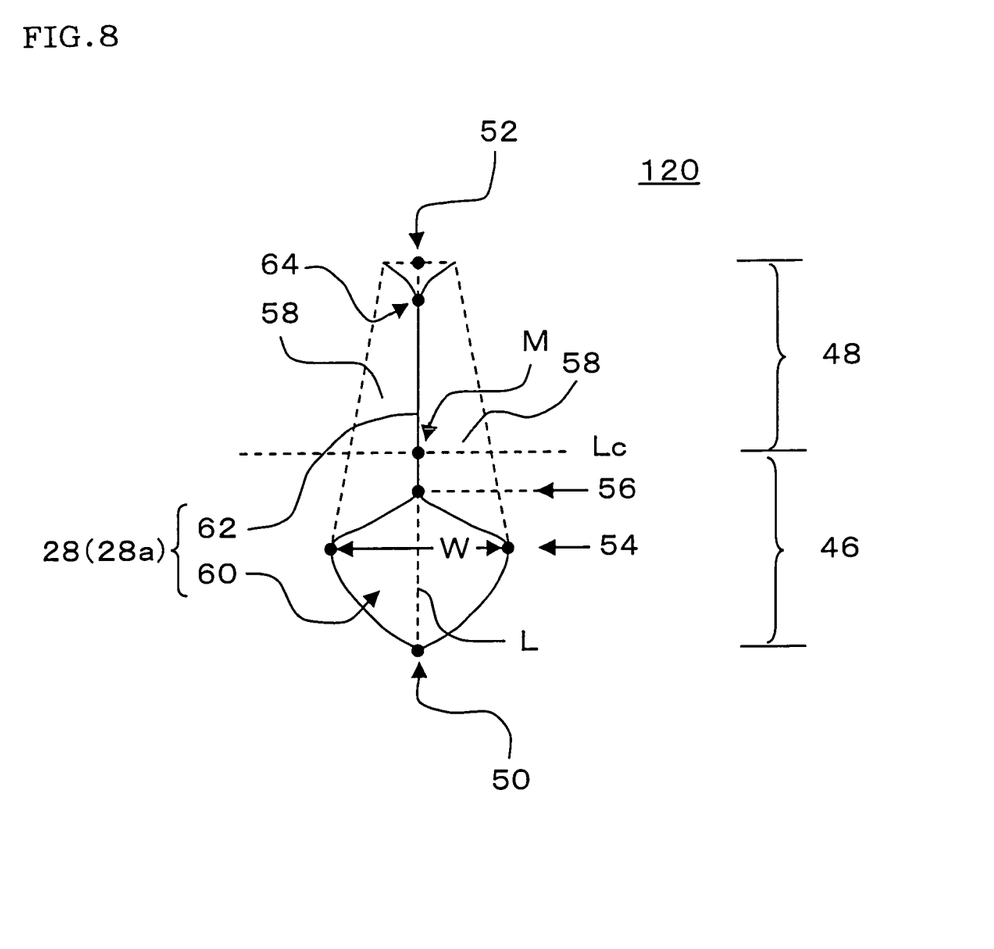
FIG. 8 is a partially enlarged view illustrating still yet another embodiment of the disposable diaper according to the present invention, enlarging the stool passing opening of the disposable diaper.

A disposable diaper 120 illustrated in FIG. 8 is another example in which the stool passing opening 28*a* has such a shape that the hole 60 and the slit 62 are combined and that the slit 62 is formed to connect with the back body side of the hole 60. In this example, however, the slit 62 is shaped to diverge in two directions from a diverging point 64 which is located at the side of the rear end 52 of the opening.

With the slit of the above-described shape, the area of the flap portions 58 can be made larger than in the disposable diaper 110 illustrated in FIG. 7. Thus, the opening area of the posterior region 48 at the time of passage of the stool can be made relatively large. The stool passing opening of this shape is preferable in that the stool once passed through the stool passing opening 28*a* is almost completely blocked by the flap portions 58, as in the case of the disposable diaper 110 illustrated in FIG. 7, and that the stool can more easily pass through the stool passing opening 28*a*.

It is preferable in the disposable diaper according to the present invention that the maximum opening portion of the stool passing opening is located at a position corresponding to the position of the anus of the wearer. The stool passing opening is formed at the crotch part, as described above, and it is preferable to form the maximum opening portion at the position corresponding to the position of the anus of the wearer because of the advantage that the stool discharged by the wearer can more easily pass through the opening.

The skin contact sheet may be formed with a urine passing opening in a region toward the front body side from the stool passing opening. That is, it is preferable that the skin contact sheet is formed with the stool passing opening and the urine passing opening, as the openings.

With the formation of the urine passing opening as described above, it is possible to cause the urine discharged by the wearer to securely flow into the inside of the skin contact sheet through the opening. Thereby, it is possible to effectively prevent the urine from diffusing down the skin contact sheet and leaking sideward from the leg-surrounding openings and the like of the diaper. For instance, the disposable diaper 1 illustrated in FIG. 2 is an example in which, in addition to the stool passing opening 28*a* of the approximately anchor shape, a urine passing opening 28*b* of an oval shape is further formed on the skin contact sheet 24 as the opening 28. In this example, the stool passing opening 28*a* is formed at a portion corresponding to the crotch part 4 of the disposable diaper 1, and the urine passing opening 28*b* is formed at a portion toward the front body part 2 from the stool passing opening 28*a*.

In the case in which two openings (i.e., the stool passing opening and the urine passing opening) are formed, as in the above-described case, it is preferable to provide a separation wall for dividing the space between the skin contact sheet and the top sheet into a space communicating with the stool passing opening and a space communicating with the urine passing opening.

If the urine and the stool are mixed, ammonia is generated and alkalinizes the surrounding environment. Then, an enzyme included in the stool is strongly activated in an alkaline atmosphere, and the enzyme and ammonia inflame a weakened part of the skin. Thereby, the diaper rash occurs. This mechanism is reported by Kazuya Yamamoto in Hifu Rinsho (Clinical Dermatology) 1998, vol. 30, pp 949-956. With the provision of the above-described separation wall, the urine discharged by the wearer can be absorbed and retained separately from the stool. As a result, the urine and the stool are not easily mixed, and the diaper rash can be effectively prevented.

It is preferable that a stretchable member (i.e., the opening stretchable members) is placed around the outer periphery of the opening. With the provision of the opening stretchable member, the skin contact sheet is applied with tension and thus becomes elastic. This contributes to an advantage that the skin contact sheet can be prevented from being crushed and sinking toward the top sheet, and that the skin contact sheet can easily come into contact with the skin of the wearer. Further, with the provision of the opening stretchable member, it is possible to generate force for causing the skin contact sheet to contract and causing the top sheet, the absorber, and the back sheet to bend toward the downside (i.e., toward the exterior covering member). Therefore, the skin contact sheet can be kept spaced from the top sheet, and the skin contact sheet and the top sheet can be definitely separated from each other. Further, when the stool passing opening contracts, the opening area of the posterior region becomes smaller than in a state in which the stool passing opening does not contract, or the posterior region may be closed in some cases. Therefore, the adherence of the stool to the gluteal groove can be more effectively suppressed.

As the material for the opening stretchable member, stretchable materials used in conventional disposable diapers can be preferably used. Specifically, the material may be a rubber thread or a flat rubber string made of a natural rubber or a synthetic rubber (e.g., urethane rubber), a stretchable net, a stretchable film, stretchable foam (e.g., urethane foam), or the like.

There is no particular restriction on the arrangement pattern of the opening stretchable member, as long as the pattern allows the exertion of the above-described effects. To definitely apply the stretching force to the opening, however, it is preferable that the opening stretchable member is arranged in such a pattern to surround the peripheral rim of the opening. For example, it is preferable to arrange the opening stretchable member in such a pattern as a circular pattern, an oval pattern, or a rhombic pattern to surround the peripheral rim of the opening.

In another preferable embodiment, two opening stretchable members are used as the opening stretchable members and arranged in such a pattern to cross at least one point anterior or posterior to the opening so as to surround a part of the peripheral rim of the opening. With the opening stretchable members arranged in such a pattern, the opening stretchable members can be continuously arranged in the anteroposterior direction of the diaper. This is preferable in view of the advantage that the continuous manufacture of disposable diapers can be easily performed.

For example, in the disposable diaper 1 illustrated in FIG. 2, two opening stretchable members 30*a* and 30*b* are used as the opening stretchable members 30 and arranged in such a pattern to cross at a point P between the stool passing opening 28a and the urine passing opening 28b so as to surround a part of the peripheral rim of each of the stool passing opening 28a and the urine passing opening 28b. With the opening stretchable members 30a and 30b arranged in such a pattern, it is possible to easily manufacture an absorbent member continuum in which the absorbent member 14 is continuously arranged in the longitudinal direction.

Further, in the disposable diaper 1 illustrated in FIG. 2, the opening stretchable members 30a and 30b are arranged to cross at the center of the crotch part 4. With this arrangement, the stretching force in the width direction (i.e., the lateral direction of the diaper) can be applied more at the crotch part 4 (i.e., the proximity of the point P) than at the front body part 2 or the back body part 6 of the diaper. Therefore, there is an effect of making the skin of the wearer come into closer contact with a portion of the skin contact sheet 24 between the stool passing opening 28a and the urine passing opening 28b, which tends to sag with relative ease. Furthermore, in the disposable diaper 1 illustrated in FIG. 2, the opening stretchable members 30a and 30b do not cross at other points than the center point P of the crotch part 4. Thus, the opening stretchable members 30a and 30b are arranged in such a pattern that a part of the peripheral rim of the stool passing opening 28a at the side of the back body part 6 and a part of the peripheral rim of the urine passing opening 28b at the side of the front body part 2 are open. With this arrangement, portions of the skin contact sheet 24 at the sides of front body part 2 and the back body part 6 do not come into excessively close contact with the skin of the wearer, and thus the breathability can be ensured. Accordingly, perspiration due to the contact of the skin contact sheet is suppressed, and the stuffiness and the skin trouble attributable to the sweat can be effectively prevented.

The opening stretchable member as described above is fixed to the skin contact sheet with an adhesive agent or another medium. The method of fixing the opening stretchable member may be bonding with a hot-melt adhesive agent or another adhesive agent of high fluidity, or welding with heat or ultrasound such as heat-sealing, for example.

To apply sufficient stretching force to the opening, it is preferable to fix the opening stretchable member with the opening stretchable member stretched. For example, if the opening stretchable member is a natural rubber or a synthetic rubber, it is preferable to fix the opening stretchable member with the opening stretchable member stretched by 100 to 400%, and more preferably by 200 to 300%. With the opening stretchable member fixed with the stretching rate of the above range, it is possible to apply the sufficient stretching force to the opening and to prevent the opening from unnecessarily contracting.

There is no particular restriction on the method of arranging the opening stretchable member. However, as in the case of the disposable diaper 1 illustrated in FIG. 3, for example, it is preferable to form the skin contact sheet 24 by pasting together two sheet members (i.e., an upper sheet 24a and a liner sheet 24b), and to place the opening stretchable members 30a and 30b to be sandwiched between the upper sheet 24a and the liner sheet 24b. The use of this arrangement method is preferable in that the stretching force can be applied to the skin contact sheet by the minimum necessary stretchable members.

The method of fixing the skin contact sheet includes, for example, (1) a method of fixing the skin contact sheet 24 such that the skin contact sheet 24 is inserted in portions where sheet members 32a and 32b, which form standing gathers 26a and 26b, respectively, are pasted with the top sheet 18 (or the back sheet 20), as in the case of the disposable diaper 1 illustrated in FIG. 3, and (2) a method of fixing the skin contact sheet to portions on the inside surfaces of the standing gathers between the upper edges and the lower edges (i.e., standing lines) of the standing gathers. Alternatively, the skin contact sheet may be fixed in an inside region encompassed by the pair of the standing gathers without being in contact with the standing gathers. For example, there is (3) a method of fixing the skin contact sheet in portions where the top sheet and the back sheet of the absorbent member are pasted together (i.e., so-called flap portions) within the region encompassed by the standing gathers. The method (1) is preferable among the above methods in that the method is highly effective in making the skin contact sheet in close contact with the skin of the wearer.

[1-2] The absorber: The absorber is a member for absorbing and retaining the urine of the wearer. The absorber is made of an absorbent material due to the need to absorb and retain the urine and the body fluid of the wearer.

The absorbent material forming the absorber includes conventionally known absorbent materials usually used in the disposable diaper and other absorbent products, such as fluff pulp, super absorbent polymer (hereinafter refereed to as SAP), and a hydrophilic sheet, for example. It is preferable to use wood pulp or non-wood pulp fibrillated into floc as the fluff pulp, to use sodium polyacrylate as the SAP, and to use tissue, an absorbent paper, or a hydrophilicized nonwoven fabric as the hydrophilic sheet.

Each of these absorbent materials is usually used in the form of a single-layer mat or a multiple-layer mat. In such a case, a single type of the above absorbent materials may be independently used, or two or more types of the absorbent materials may be used in combination. In particular, it is preferable to use approximately 10 to 500 parts by mass of the SAP with respect to 100 parts by mass of the fluff pulp. In this case, the SAP may be evenly mixed in each of the fluff pulp mats or may be placed in layers between a plurality of fluff pulp layers.

It is preferable that the absorber is interposed between at least parts of the top sheet and the back sheet. Usually, the absorber is sandwiched between the top sheet and the back sheet, and the peripheral rim of the absorber is sealed by adhesion so that the absorber is interposed between the top sheet and the back sheet. Therefore, the flap portions, in which the absorber is not interposed between the top sheet and the back sheet, are formed around the peripheral rim of the absorber.

It is preferable the entire absorber is wrapped by a hydrophilic sheet. This structure provides an advantage in that the SAP is prevented from leaking from the absorber and that the absorber is provided with the shape stability.

There is no particular restriction on the shape of the absorber. The shape of the absorber includes the shapes used in the conventional disposable diaper and other absorbent products, such as a rectangular shape, an hourglass shape, a calabash shape, and a T-shape, for example.

[1-3] The top sheet: The top sheet is a sheet disposed to cover the upper surface of the absorber (i.e., the surface at the side of the skin of the wearer when the diaper is applied to the wearer). The top sheet is at least partially (i.e., a part or the entirety of the top sheet is) made of a liquid permeable material due to the need to cause the absorber disposed at the side of the lower surface of the top sheet to absorb the urine of the wearer.

The liquid permeable material forming the top sheet includes a woven fabric, a nonwoven fabric, and a porous film, for example. In particular, it is preferable to use a hydrophilicized nonwoven fabric made of a thermoplastic resin such as polypropylene, polyethylene, polyester, or nylon.

The top sheet may be formed by a single sheet material. Alternatively, the top sheet may be formed by a plurality of sheet materials. For example, in a frequently used embodiment of a tape-type diaper later described, a top sheet (i.e., a center sheet) made of a liquid permeable material is disposed at the center of the diaper, and another top sheet (i.e., a side sheet) made of a water repellent material is disposed at side flap portions of the diaper.

[1-4] The back sheet: The back sheet is a sheet disposed to cover the lower surface of the absorber (i.e., the surface at the side of the clothes of the wearer when the diaper is applied to the wearer). The back sheet is made of a liquid impermeable material due to the need to prevent the urine of the wearer from leaking to the outside of the diaper.

The liquid impermeable material forming the back sheet includes, for example, a liquid impermeable film made of a resin such as polyethylene. In particular, it is preferable to use a microporous polyethylene film. The microporous polyethylene film is formed with a multitude of micro holes of a size of 0.1 to a few micrometers. The microporous polyethylene film is liquid impermeable but moisture permeable, and thus has an advantage of capable of preventing the inside of the diaper from becoming stuffy.

A sheet member (i.e., a cover sheet) may be pasted to the outer surface of the back sheet. The cover sheet is used to reinforce the back sheet and to improve the hand feeling (i.e., the tactile feeling) of the back sheet.

The material forming the cover sheet includes a woven fabric and a nonwoven fabric, for example. In particular, it is preferable to use a dry or wet nonwoven fabric made of a thermoplastic resin such as polyethylene, polypropylene, or polyester.

[1-5] The absorbent member: In the two-piece-type and pants-type diaper, the top sheet, the back sheet, and the absorber are formed as one member, i.e., the "absorbent member" having the absorbing and retaining function, and the absorbent member is joined with the exterior covering member, which has been manufactured separately from the absorbent member. Thereby, the disposable diaper is formed. In the absorbent member, as in the case of a sanitary napkin or the like, the top sheet and the back sheet are disposed on the upper surface and the lower surface of the absorber, respectively, so that the absorber is interposed between the top sheet and the back sheet. For example, the disposable diaper 1 illustrated in FIG. 3 is an example in which the absorbent member 14 is formed by inserting the absorber 22 between the top sheet 18 and the back sheet 20 and adhering and sealing the peripheral rim of the absorber 22 to make the absorber 22 interposed between the top sheet 18 and the back sheet 20.

The absorbent member is formed into such a size to cover at least the crotch part of the diaper. To ensure the leakage preventing effect, however, it is preferable to form the absorbent member into such a size to cover not only the crotch part but also a part of the front body part and the back body part. The absorbent member can be fixed to the exterior covering member with the hot-melt adhesive agent or the like, for example.

[1-6] The exterior covering member: The exterior covering member is a member having the fitting function of covering the body of the wearer. Specifically, the exterior covering member is a sheet-shaped member for forming respective parts of the front body part, the crotch part, and the back body part.

In the two-piece-type and pants-type diaper, the absorbing and retaining function of absorbing and retaining the excrement of the wearer is performed solely by the absorbent member, and thus there is no need to use the liquid impermeable material as the material forming the exterior covering member. The material forming the exterior covering member includes, for example, a nonwoven fabric formed by a synthetic fiber of polyethylene, polypropylene, polyester, or another thermoplastic resin.

The exterior covering member is fixed, with such members as the leg-surrounding stretchable members inserted in the exterior covering member. In many cases, therefore, the exterior covering member is formed by pasting together two or more nonwoven fabrics. For example, the disposable diaper 1 illustrated in FIGS. 1 to 3 is an example in which the exterior covering member 16 is formed by two nonwoven fabrics, and leg-surrounding stretchable members 40, waist-surrounding stretchable members 42, and belly-surrounding stretchable members 44 are inserted and fixed between the two nonwoven fabrics.

[1-7] The respective stretchable members: In the pants-type disposable diaper, the leg-surrounding stretchable members and the waist-surrounding stretchable members are generally provided, and it is preferable to further provide the belly-surrounding stretchable members.

The leg-surrounding stretchable members are stretchable members placed along the respective leg-surrounding openings. With the provision of the leg-surrounding stretchable members, highly stretchable gathers (i.e., leg gathers) can be formed around the leg-surrounding openings. Accordingly, a clearance gap is not easily formed around the legs, and the leakage of the urine from the leg-surrounding openings can be effectively prevented.

The waist-surrounding stretchable members are stretchable members placed along the waist-surrounding opening. With the provision of the waist-surrounding stretchable members, a highly stretchable gather (i.e., a waist gather) can be formed around the waist-surrounding opening. With the waist gather, a clearance gap is not easily formed around the waist, and the leakage of the urine from the area around the waist can be prevented. Further, the fittedness of the diaper to the wearer is improved, and thus the diaper is prevented from slipping down.

The belly-surrounding stretchable members are stretchable members placed in a portion between the waist-surrounding opening and the leg-surrounding openings (i.e., a portion corresponding to the area around the belly of the wearer). With the provision of the belly-surrounding stretchable members, a highly stretchable tummy gather can be formed around the belly of the wearer. Coupled with the waist gather, the tummy gather can further improve the fittedness of the diaper and the effect of preventing the slide down of the diaper.

The disposable diaper 1 illustrated in FIGS. 1 and 2 is an example in which a plurality of the leg-surrounding stretchable members 40 are placed around the peripheral rims of the leg-surrounding openings 12*a* and 12*b*, and a plurality of the waist-surrounding stretchable members 42 are placed around the peripheral rim of the waist-surrounding opening 10 so as to surround the waist-surrounding opening 10. Further, a plurality of the belly-surrounding stretchable members 44 are placed in the portion between the waist-surrounding opening 10 and the leg-surrounding openings 12*a* and 12*b* (i.e., the portion corresponding to the area around the belly of the wearer) so as to surround the belly of the wearer.

Each of these stretchable members can employ a similar structure to the structure used in the opening stretchable member described above. Further, the material forming the stretchable member, the elongation rate of the material, the elongated state of the stretchable member when the stretchable member is fixed, and the like can be determined in consideration of such factors as the extent of contraction of the gather.

[1-8] The standing gathers: The disposable diaper may include the standing gathers for preventing the sideward leakage of the urine discharged by the wearer. The standing gathers are members for preventing the sideward leakage of the urine discharged by the wearer, and are leakage preventing walls structured to stand three-dimensionally. With the provision of the standing gathers, even if the urine is discharged on the skin contact sheet and diffuses down the skin contact sheet, the standing gathers function as breakwaters, and the leakage from the leg-surrounding openings and the like of the diaper (i.e., the so-called sideward leakage) can be effectively prevented. Incidentally, the word "standing gather(s)" may be expressed as "barrier cuff".

The standing gather can employ a similar structure to the structure used in the conventional disposable diaper and other absorbent products. For example, by providing a stretchable member (i.e., a standing gather stretchable member) on a part of a water repellant sheet member, a gather (i.e., folds) formed on the sheet member by the standing gather stretchable member can be preferably used.

The disposable diaper 1 illustrated in FIGS. 2 and 3 is an example wherein a pair of the standing gathers 26a and 26b are formed by pasting the sheet members 32a and 32b, which are completely separate from the top sheet 18 and the back sheet 20, to the opposite side edges of the absorbent body 14 such that the sheet members 32a and 32b can stand three-dimensionally from the standing lines 38. In this example, an edge portion of each of the sheet members 32a and 32b (i.e., an edge portion corresponding to the upper end edge 34 of each of the standing gather 26a and 26b) is folded, and the folded portion tucks therein the two standing gather stretchable members 36a and 36b or the two standing gather stretchable members 36c and 36d.

[2] The manufacturing method: An embodiment of the method of manufacturing the disposable diaper according to the present invention will now be described, taking an example in which the disposable diaper 1 illustrated in FIGS. 1 to 4 (i.e., the two-piece-type and pants-type diaper) is manufactured.

[2-1] The manufacture of the absorbent member: The absorber 22 wrapped by a hydrophilic sheet is disposed on the upper surface of the back sheet 20, and the top sheet 18 is disposed on the upper surface of the absorber 22. Then, the peripheral rim of the absorber 22 is sealed by adhesion, sandwiched by the top sheet 18 and the back sheet 20. Thereby, the absorbent member 14 is obtained.

[2-2] The manufacture of the skin contact sheet: The upper sheet 24a is pasted on the upper surface of the liner sheet 24b, with the two opening stretchable members 30a and 30b arranged in a predetermined pattern. In this case, the two opening stretchable members 30a and 30b are arranged in such a pattern to cross at the point P between the stool passing opening 28a and the urine passing opening 28b, which are later formed, and to surround a part of the peripheral rim of each of the stool passing opening 28a and the urine passing opening 28b.

Subsequently, the stool passing opening 28a and the urine passing opening 28b are formed into respective predetermined shapes on the liner sheet 24b and the upper sheet 24a, which have been pasted together. Thereby, the double-layer structured skin contact sheet 24 is obtained in which the two opening stretchable members 30a and 30b are arranged in such a pattern to cross at the point P between the stool passing opening 28a and the urine passing opening 28b, and to surround a part of the peripheral rim of each of the stool passing opening 28a and the urine passing opening 28b.

[2-3] The manufacture of the standing gathers: One edge portion of the sheet member 32a or 32b is folded, and the two the standing gather stretchable members 36a and 36b or 36c and 36d are tucked in and pasted to the obtained folded portion. Thereby, the standing gather 26a or 26b is obtained.

[2-4] The provision of the skin contact sheet and the like to the absorbent member: The skin contact sheet 24 is pasted to a surface of the top sheet 18 which forms the absorbent member 14, and then each of the standing gathers 26a and 26b is pasted to the corresponding side edge of the absorbent member 14 and the skin contact sheet 24, with each of the standing gathers 26a and 26b tucking therein the corresponding side edge of the absorbent member 14 and the skin contact sheet 24.

[2-5] The manufacture of the exterior covering member: Two nonwoven fabrics for forming the exterior covering member 16 are first prepared. Then, the waist-surrounding stretchable members 42, the belly-surrounding stretchable members 44, and the leg-surrounding stretchable members 40 are disposed and fixed by adhesion on the upper surface of one of the nonwoven fabrics. Thereafter, the other one of the nonwoven fabrics is layered on and fixed to the upper surface of the one of the nonwoven fabrics. Thereby, the exterior covering member 16 is obtained in which the waist-surrounding stretchable members 42, the belly-surrounding stretchable members 44, and the leg-surrounding stretchable members 40 are interposed between the two nonwoven fabrics.

[2-6] The manufacture of the disposable diaper: The absorbent member 14 is disposed at and fixed to the proximity of the crotch part of the exterior covering member 16. Then, the exterior covering member 16 is folded in half such that the front body part 2 and the back body part 6 are aligned with each other, with the absorbent member 14 on the inside of the folded exterior covering member 16. Thereafter, the front body part 2 and the back body part 6 are joined by such a method as heat-sealing, and the joining parts 8 are formed. Thereby, the disposable diaper 1 illustrated in FIGS. 1 to 4 is manufactured.

The above-described sequence of processes can be continuously performed by a mechanical method or apparatus. For example, with a method or apparatus for continuously sending out a long sheet material or a long stretching material by a roller, for example, the continuous manufacture of the disposable diaper can be performed. This contributes to the improvement of the productivity.

The scope of application of the present invention: The scope of application of the disposable diaper according to the present invention is not limited to the above-described two-piece-type and pants-type diaper, but the present invention is also applicable to a one-piece-type and pants-type diaper and a tape-type diaper, for example. That is, these diapers can also have the effects of the disposable diaper according to the present invention, if the skin contact sheet is disposed above the surface of the top sheet and is formed with the stool passing opening of a predetermined shape.

The "one-piece-type diaper" refers to a type of diaper which includes a top sheet, a back sheet, and an absorber, similarly to the two-piece-type diaper, but in which the absorber having the absorbing and retaining function is interposed (i.e., embedded) between the top sheet and the back sheet and is integrated with the top sheet and/or the back sheet having the fitting function.

The "tape-type diaper" refers to a disposable diaper which includes a top sheet, a back sheet, an absorber interposed between at least parts of the two sheets, and tape fasteners for fitting the diaper, and in which a front body part and a back body part can be fixed to each other by the tape fasteners. The "tape-type diaper" also includes the "one-piece-type" and the "two-piece-type," and the disposable diaper according to the present invention is applicable to either type of the tape-type diaper.

The disposable diaper according to the present invention can be preferably used as the diaper for an infant or an adult such as an elder or disabled person who needs nursing care. Further, the disposable diaper according to the present invention can effectively prevent the mixture of the urine and the stool. Thus, the occurrence of the diaper rash attributable to the mixture of the urine and the stool can be effectively suppressed. Accordingly, the disposable diaper according to the present invention can be preferably used particularly as the disposable diaper for an infant who has a sensitive skin and thus frequently has skin trouble.

What is claimed is:

1. A disposable diaper comprising:
    an absorber;
    a top sheet disposed to cover an upper surface of the absorber and at least partially formed of a liquid permeable material;
    a back sheet disposed to cover a lower surface of the absorber and formed of a liquid impermeable material; and
    a skin contact sheet disposed above the top sheet so that a space is defined between at least a portion of a bottom surface of the skin contact sheet and an upper surface of the top sheet, wherein the skin contact sheet has a single stool passing opening formed therein in a crotch part thereof, that is capable of passing a stool therethrough and into the space, and wherein the skin contact sheet also has a single urine passing opening formed therein in a front body part thereof, which is separated from the single stool passing opening, and which is capable of passing urine therethrough and into the space;
    wherein a shape of the stool passing opening includes an opening area in a posterior region, which is located posterior to a centerline of the stool passing opening in the anteroposterior direction of the stool passing opening, that is smaller than an opening area in an anterior region, which is located anterior to the centerline of the stool passing opening, and wherein flap portions are provided at side edges of the stool passing opening, the flap portions being capable of preventing stool passed through the stool passing opening and into the space from contacting a wearer of the disposable diaper.

2. The disposable diaper according to claim 1,
    wherein the stool passing opening comprises a hole combined with a slit that connects with a back body side of the hole.

3. The disposable diaper according to claim 1,
    wherein the shape of the opening area in the anterior region of the stool passing opening includes a maximum opening portion in which an opening width of the stool passing opening is the greatest.

4. The disposable diaper according to claim 3,
    wherein the opening width of the stool passing opening decreases from the maximum opening portion toward a rear end of the stool passing opening.

5. The disposable diaper according to claim 3,
    wherein the stool passing opening comprises a hole combined with a slit that connects with a back body side of the hole.

6. The disposable diaper according to claim 3,
    wherein the maximum opening portion of the stool passing opening is located at a position corresponding to a position of the anus of a wearer of the disposable diaper.

7. The disposable diaper according to claim 4,
    wherein a decrease in a rate of the opening width of the stool passing opening is large in a segment from the maximum opening portion to a predetermined inflection point, and small in a segment from the inflection point to the rear end of the stool passing opening.

8. The disposable diaper according to claim 4,
    wherein the opening width of the stool passing opening decreases at a constant rate from the maximum opening portion to the rear end of the stool passing opening.

9. The disposable diaper according to claim 4,
    wherein the stool passing opening comprises a hole combined with a slit that connects with a back body side of the hole.

10. The disposable diaper according to claim 4,
    wherein the maximum opening portion of the stool passing opening is located at a position corresponding to the position of the anus of a wearer of the disposable diaper.

11. The disposable diaper according to claim 7,
    wherein the stool passing opening comprises a hole combined with a slit that connects with a back body side of the hole.

12. The disposable diaper according to claim 7,
    wherein the maximum opening portion of the stool passing opening is located at a position corresponding to the position of the anus of a wearer of the disposable diaper.

13. The disposable diaper according to claim 8,
    wherein the stool passing opening comprises a hole combined with a slit that connects with a back body side of the hole.

14. The disposable diaper according to claim 8,
    wherein the maximum opening portion of the stool passing opening is located at a position corresponding to the position of the anus of a wearer of the disposable diaper.

* * * * *